(12) United States Patent
Kerr et al.

(10) Patent No.: US 9,987,079 B2
(45) Date of Patent: *Jun. 5, 2018

(54) SURGICAL INSTRUMENT WITH FIBER BRAGG GRATING

(71) Applicant: COVIDIEN LP, Mansfield, MA (US)

(72) Inventors: Duane E. Kerr, Loveland, CO (US); William H. Nau, Jr., Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/648,571

(22) Filed: Jul. 13, 2017

(65) Prior Publication Data

US 2017/0303996 A1    Oct. 26, 2017

Related U.S. Application Data

(63) Continuation of application No. 15/194,040, filed on Jun. 27, 2016, now Pat. No. 9,707,032, which is a (Continued)

(51) Int. Cl.
| | |
|---|---|
| *A61B 18/18* | (2006.01) |
| *A61B 18/14* | (2006.01) |
| *G01K 11/32* | (2006.01) |
| *G01L 1/24* | (2006.01) |
| *A61B 18/12* | (2006.01) |

(Continued)

(52) U.S. Cl.
CPC ...... *A61B 18/1445* (2013.01); *A61B 18/1206* (2013.01); *A61B 18/1482* (2013.01); *A61B 90/06* (2016.02); *G01K 11/3206* (2013.01);

*G01L 1/246* (2013.01); *A61B 2017/00057* (2013.01); *A61B 2018/0063* (2013.01); *A61B 2018/00077* (2013.01); *A61B 2018/00095* (2013.01); *A61B 2018/00178* (2013.01); *A61B 2018/00648* (2013.01); *A61B 2018/00791* (2013.01); *A61B 2018/00797* (2013.01);
(Continued)

(58) Field of Classification Search
USPC .................................................... 606/52, 205
See application file for complete search history.

(56) References Cited

U.S. PATENT DOCUMENTS

| | | |
|---|---|---|
| 5,769,791 A | 6/1998 | Benaron et al. |
| 6,682,528 B2 | 1/2004 | Frazier et al. |

(Continued)

OTHER PUBLICATIONS

International Search Report from PCT Appl. No. PCT/US2013/045208 dated Apr. 3, 2014.

*Primary Examiner* — Nicole F Johnson (57) ABSTRACT

A surgical instrument includes an end effector including first and second jaw members movable relative to one another between a first, spaced-apart position and a second position proximate tissue. In the second position, the jaw members cooperate to grasp tissue therebetween. A first optical fiber is disposed within the first jaw member and is configured to provide a first signal, and a second optical fiber is disposed within the first jaw member and is configured to provide a second signal. A controller is coupled to the first and second fibers and is configured to determine the temperature and the strain of the first jaw member as a function of the first and second signals, respectively.

14 Claims, 6 Drawing Sheets

Related U.S. Application Data continuation of application No. 14/808,922, filed on Jul. 24, 2015, now Pat. No. 9,375,265, which is a continuation of application No. 13/803,884, filed on Mar. 14, 2013, now Pat. No. 9,113,904.

(60) Provisional application No. 61/673,654, filed on Jul. 19, 2012.

(51) Int. Cl.
 *A61B 18/00* (2006.01)
 *A61B 90/00* (2016.01)
 *A61B 17/00* (2006.01)

(52) U.S. Cl.
 CPC ... *A61B 2018/126* (2013.01); *A61B 2090/064* (2016.02); *A61B 2562/0266* (2013.01)

(56) References Cited

U.S. PATENT DOCUMENTS

| | | |
|---|---|---|
| 7,156,846 B2 | 1/2007 | Dycus et al. |
| 7,393,354 B2 | 7/2008 | Buchman, II et al. |
| 7,553,686 B2 | 6/2009 | George et al. |
| 8,298,232 B2 | 10/2012 | Unger |
| 9,113,904 B2 | 8/2015 | Kerr et al. |
| 2006/0224053 A1 | 10/2006 | Black et al. |
| 2007/0060847 A1 | 3/2007 | Leo et al. |
| 2007/0078484 A1 | 4/2007 | Talarico et al. |
| 2008/0077200 A1 | 3/2008 | Bendett et al. |
| 2008/0125775 A1 | 5/2008 | Morris |
| 2009/0287092 A1 | 11/2009 | Leo et al. |
| 2010/0217258 A1* | 8/2010 | Floume ............... A61B 5/0059 606/34 |
| 2010/0331838 A1* | 12/2010 | Ibrahim ............... A61B 17/28 606/52 |
| 2011/0137337 A1* | 6/2011 | van den Dool ....... A61B 17/29 606/205 |
| 2012/0179068 A1* | 7/2012 | Leo .................... A61B 5/0084 600/587 |
| 2012/0296317 A1 | 11/2012 | Chernov et al. |
| 2012/0296323 A1 | 11/2012 | Chernov et al. |
| 2012/0296324 A1 | 11/2012 | Chernov et al. |

\* cited by examiner

SURGICAL INSTRUMENT WITH FIBER BRAGG GRATING

CROSS-REFERENCE TO RELATED APPLICATIONS

This application is a continuation application of U.S. patent application Ser. No. 15/194,040, filed on Jun. 27, 2016, now U.S. Pat. No. 9,707,032, which is a continuation application of U.S. patent application Ser. No. 14/808,922, filed on Jul. 24, 2015, now U.S. Pat. No. 9,375,265, which is a continuation application of U.S. patent application Ser. No. 13/803,884, filed on Mar. 14, 2013, now U.S. Pat. No. 9,113,904, which claims the benefit of and priority to U.S. Provisional Application Ser. No. 61/673,654, filed on Jul. 19, 2012, the entire contents of each of which are incorporated by reference herein.

BACKGROUND

1. Technical Field

The present disclosure relates generally to the field of surgical instruments. In particular, the disclosure relates to an electrosurgical forceps having improved sensors.

2. Background of Related Art

Instruments such as electrosurgical forceps are commonly used in open and endoscopic surgical procedures to coagulate, cauterize and seal tissue. Such forceps typically include a pair of jaws that can be controlled by a surgeon to grasp targeted tissue, such as, e.g., a blood vessel. The jaws may be approximated to apply a mechanical clamping force to the tissue, and are associated with at least one electrode to permit the delivery of electrosurgical energy to the tissue. The combination of the mechanical clamping force and the electrosurgical energy has been demonstrated to join adjacent layers of tissue captured between the jaws. When the adjacent layers of tissue include the walls of a blood vessel, sealing the tissue may result in hemostasis, which may facilitate the transection of the sealed tissue. A detailed discussion of the use of an electrosurgical forceps may be found in U.S. Pat. No. 7,255,697 to Dycus et al.

A bipolar electrosurgical forceps typically includes opposed electrodes disposed on clamping faces of the jaws. The electrodes are charged to opposite electrical potentials such that an electrosurgical current may be selectively transferred through tissue grasped between the electrodes. To effect a proper seal, particularly in relatively large vessels, two predominant mechanical parameters must be accurately controlled: the pressure applied to the vessel, and the gap distance established between the electrodes.

Both the pressure and gap distance influence the effectiveness of the resultant tissue seal. If an adequate gap distance is not maintained, there is a possibility that the opposed electrodes will contact one another, which may cause a short circuit and prevent energy from being transferred through the tissue. Also, if too low a force is applied the tissue may have a tendency to move before an adequate seal can be generated. The thickness of a typical effective tissue seal is optimally between about 0.001 and about 0.005 inches. Below this range, the seal may shred or tear and above this range the vessel walls may not be effectively joined. Closure pressures for sealing large tissue structures may fall within the range of about 3 $kg/cm^2$ to about 16 $kg/cm^2$.

SUMMARY

The present disclosure relates to an electrosurgical apparatus and methods for performing electrosurgical procedures. More particularly, the present disclosure relates to electrosurgically sealing tissue. As is traditional, the term "distal" refers herein to an end of the apparatus that is farther from an operator, and the term "proximal" refers herein to the end of the forceps which is closer to the operator.

According to one embodiment of the present disclosure, a surgical instrument includes an end effector including first and second jaw members movable relative to one another between a first, spaced-apart position and a second position proximate tissue. In the second position, the jaw members cooperate to grasp tissue therebetween. A first optical fiber is disposed within the first jaw member and is configured to provide a first signal, and a second optical fiber is disposed within the first jaw member and is configured to provide a second signal. A controller is coupled to the first and second fibers and is configured to determine the temperature and the strain of the first jaw member as a function of the first and second signals, respectively.

In embodiments, each of the first and second optical fibers includes at least one Bragg grating. The first optical fiber may be disposed within a first cavity defined in the first jaw member and the second optical fiber may be disposed within a second cavity defined in the first jaw member. Further, the first optical fiber may be secured within the first cavity. The second optical fiber may be unsecured within the second cavity. The first and second cavities may include a thermally and electrically conductive material. The electrically conductive material may be saline.

In embodiments, the first signal includes a first component corresponding to a temperature measurement. The second signal may include a first component corresponding to the temperature measurement and a second component corresponding to a strain measurement, wherein the first component of the first signal is substantially identical to the first component of the second signal. Additionally, the controller is configured to determine the strain measurement by removing the first component of the first signal from the second signal.

According to another embodiment of the present disclosure, a surgical instrument includes an end effector including first and second jaw members movable relative to one another between a first, spaced-apart position and a second position proximate tissue. In the second position, the jaw members cooperate to grasp tissue therebetween. A first optical fiber is unsecuredly mounted within the first jaw member and is configured to provide a first signal, and a second optical fiber is securely mounted within the second cavity and is configured to provide a second signal. A controller is coupled to the first and second fibers and is configured to determine the temperature and the strain of the first jaw member as a function of the first and second signals. Each of the first and second optical fibers may include at least one Bragg grating.

In embodiments, the first signal includes a first component corresponding to a temperature measurement. The second signal may include a first component corresponding to the temperature measurement and a second component corresponding to a strain measurement, wherein the first component of the first signal is substantially identical to the first component of the second signal.

In embodiments, the first signal includes a first component corresponding to a temperature measurement. The second signal may include a first component corresponding to the temperature measurement and a second component corresponding to a strain measurement, wherein the first component of the first signal is substantially identical to the first component of the second signal. The controller may be configured to determine the strain measurement by removing the first component of the first signal from the second signal.

According to another embodiment, a method for determining temperature and strain of a surgical end effector includes detecting a first signal from a first optical fiber unsecuredly mounted within the end effector, detecting a second signal from a second optical fiber securely mounted within the end effector, and determining at least one of temperature or strain of the end effector as a function of the first and second signals. The first signal may include a first component corresponding to a temperature measurement and the second signal may include a first component corresponding to the temperature measurement and a second component corresponding to a strain measurement, wherein the first component of the first signal is substantially identical to the first component of the second signal. The first component of the first signal from the second signal may be removed to determine the strain of the end effector.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION

The present disclosure provides for a system and method for providing a variety of sensor feedback regarding operation of an electrosurgical forceps including, but not limited to, temperature of the jaw members, pressure exerted by the jaw members, blood flow within vessels grasped by the jaw members, position and pressure of various mechanical actuation components of the forceps, identification information corresponding to the forceps. Although the feedback system according to present disclosure is described below with respect to an endoscopic forceps, the system may be utilized in a variety of surgical instruments, including but not limited to, open surgical forceps, tweezer-type devices, and the like.

Figure 1:
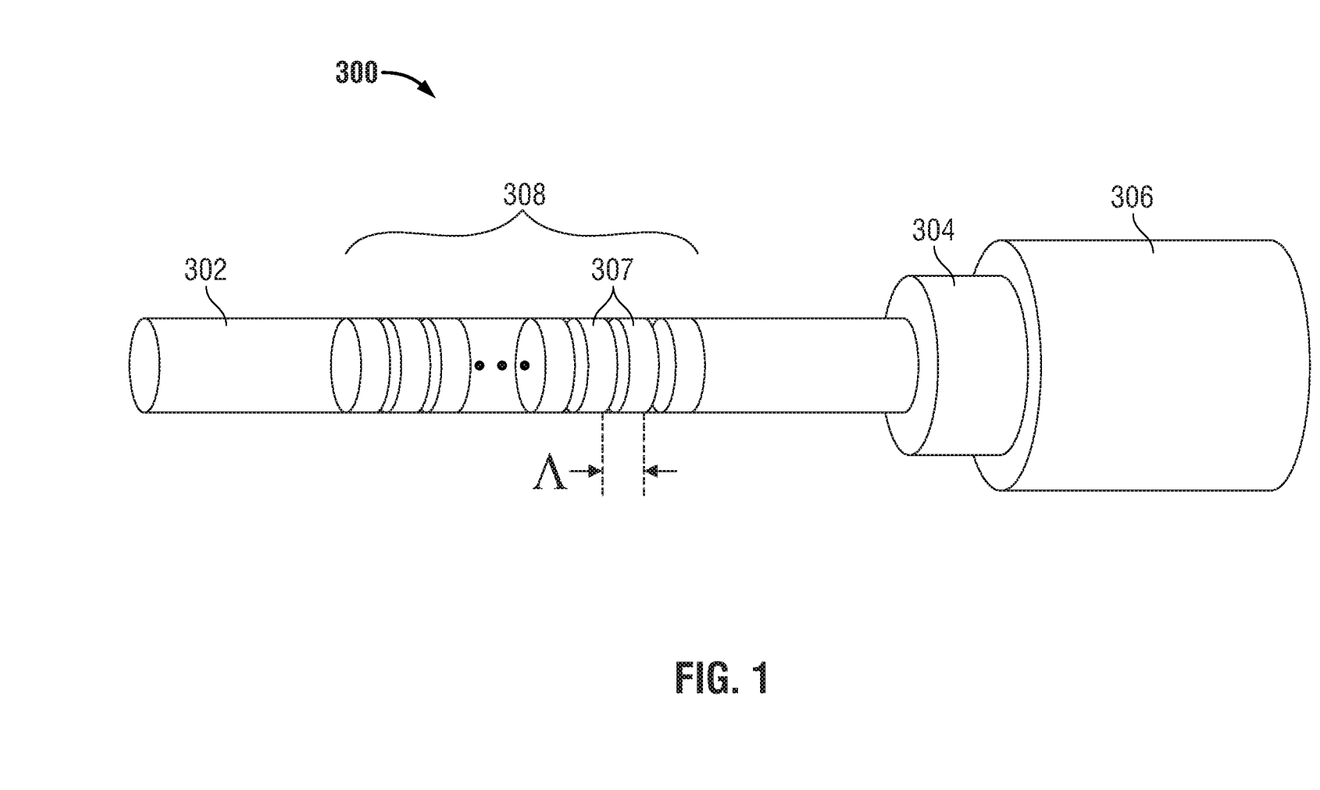
FIG. 1 is a perspective view of an optical sense fiber according to an embodiment of the present disclosure.

With reference to FIG. 1, an optical sense fiber 300 according to the present disclosure is shown. The fiber 300 includes a core 302, a cladding 304 disposed over the core 302, and a buffer coating 306 covering the cladding 304. The fiber 300 also includes one or more fiber Bragg gratings (FBG) 308 as shown in FIG. 1. Multiple gratings 308 may be written, e.g., etched, into the fiber 300 if the gratings 308 are formed in such a way as to use different wavelengths. This is particularly useful for using a single fiber to sense multiple locations within the instrument. In further embodiments, multiple fibers 300 may be included each having one or more gratings 308.

The optical sense fiber 300 may be any flexible optical fiber, such as a phosphate glass fiber. The gratings 308 include a plurality of reflection points 307 written into the fiber 300 at periodic spacing "Λ." In embodiments, the grating 308 may be written into the fiber 300 using high intensity pulses from a laser (e.g., argon fluoride excimer laser with a phase mask). As the fiber 300 undergoes mechanical strain (e.g., a change in length) due to temperature and pressure changes, the spacing Λ is modified due to stretching or contraction of the fiber 300. This allows for measurement of the effects of pressure and temperature by measuring the wavelength shift in light reflected by the reflection points 307 based on the formula (I), which is reproduced below:

$$\frac{\Delta\lambda}{\lambda_0} = k*\varepsilon + \alpha_\delta * \Delta T \tag{I}$$

In formula (I), $\Delta\lambda$ is the wavelength shift, $\lambda_0$ is the base wavelength, k is a gage factor, which is a difference between 1 and a photo-elastic coefficient, $\rho$, $\varepsilon$ is strain, $\Delta T$ is a temperature change, and $\alpha_\delta$ is a change of the refraction index. In particular, changes in temperature and strain affect (e.g., stretch or contract) the fiber 300, which in turn modifies the spacing between the gratings 308. The change in the gratings 308 affects the wavelength of the light reflected back through the fiber 300. The change in the wavelength is then used by a controller (e.g., interrogator 41a of FIG. 1) to determine the change in temperature and/or strain affecting the fiber 300.

Figure 2:
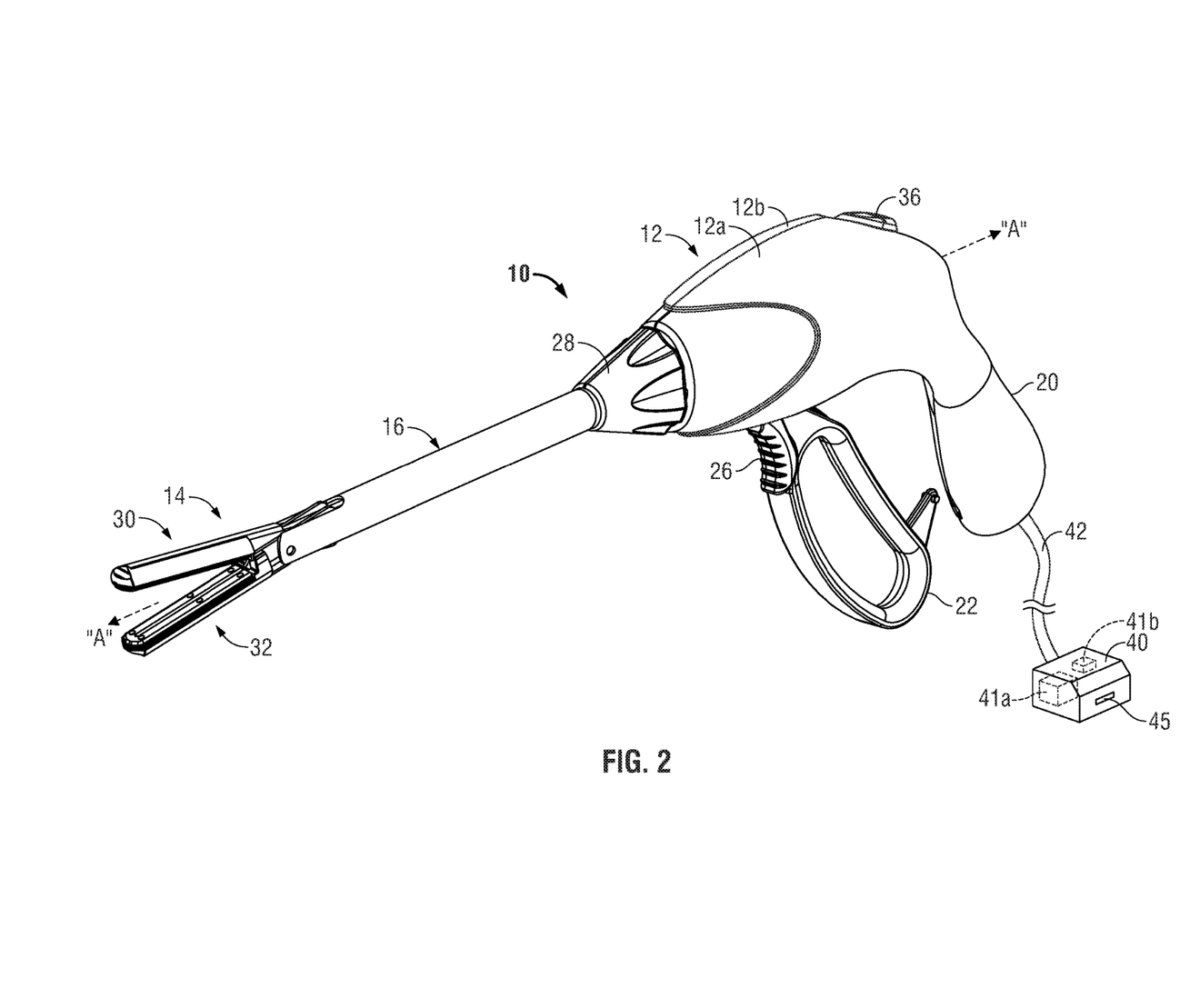
FIG. 2 is a perspective view of an electrosurgical forceps according to an embodiment of the present disclosure including a housing, an elongated shaft, and an end effector.

With reference to FIG. 2, an embodiment of an electrosurgical forceps 10 generally includes a housing 12 that supports various actuators thereon for remotely controlling an end effector 14 through an elongated shaft 16. Although this configuration is typically associated with instruments for use in laparoscopic or endoscopic surgical procedures, various aspects of the present disclosure may be practiced with traditional open instruments and in connection with endoluminal procedures as well.

The housing 12 is constructed of a left housing half 12a and a right housing half 12b. The left and right designation of the housing halves 12a, 12b refer to the respective directions as perceived by an operator using the forceps 10. The housing halves 12a, 12b may be constructed of plastic, and may be joined to one another by adhesives, ultrasonic welding or other assembly methods known in the art.

To mechanically control the end effector 14, the housing 12 supports a stationary handle 20, a movable handle 22, a trigger 26, and a rotation knob 28. The movable handle 22 is operable to move the end effector 14 between an open configuration (FIG. 3A) wherein a pair of opposed jaw members 30, 32 are disposed in spaced relation relative to one another, and a closed or clamping configuration (FIG. 3B) wherein the jaw members 30, 32 are closer together. Approximation of the movable handle 22 with the stationary handle 20 serves to move the end effector 14 to the closed configuration and separation of the movable handle 22 from the stationary handle 20 serves to move the end effector 14 to the open configuration. The trigger 26 is operable to extend and retract a knife blade 56 (see FIG. 3A) through the end effector 14 when the end effector 14 is in the closed configuration. The rotation knob 28 serves to rotate the elongated shaft 16 and the end effector 14 about a longitudinal axis A-A extending through the forceps.

To electrically control the end effector 14, the housing 12 supports a switch 36 thereon, which is operable by the user to initiate and terminate the delivery of electrosurgical energy to the end effector 14. The switch 36 is in electrical communication with a source of electrosurgical energy such as electrosurgical generator 40. The generator 40 may include devices such as the LIGASURE® Vessel Sealing Generator and the FORCETRIAD® Generator as sold by Covidien Energy-based Devices of Boulder, Colo. Electrosurgical energy may be supplied by any suitable electrosurgical generator as is known in the art. A cable 42 extends between the housing 12 and the generator 40 and includes a connector 43 (FIGS. 3 and 4) thereon such that the forceps 10 may be selectively coupled and decoupled electrically from the generator 40. One or more fibers 300 are disposed within the forceps 10, the jaw members 30, 32, and/or the connector 43 as described in further detail below with respect to FIGS. 6 and 7. The fiber 300 senses temperature and pressure within the forceps 10, the jaw members 30, 32 and other components and provides identification information of the forceps 10 to the generator 40. The generator 40 also includes an interrogator 41a coupled to the fiber 300 that decodes the optically encoded strain information from fiber 300 into electrical signals compatible with the computer control hardware of the generator 40. The generator 40 includes a controller 41b which is used to calculate temperature and forces exerted on the fiber 300 based on the formula (I). The controller 41b may be any suitable type of logic circuit, such as field programmable gate array, processor, and the like. The generator 40 also includes a receptacle 45 configured to interface with the connector 43.

Figure 3A:
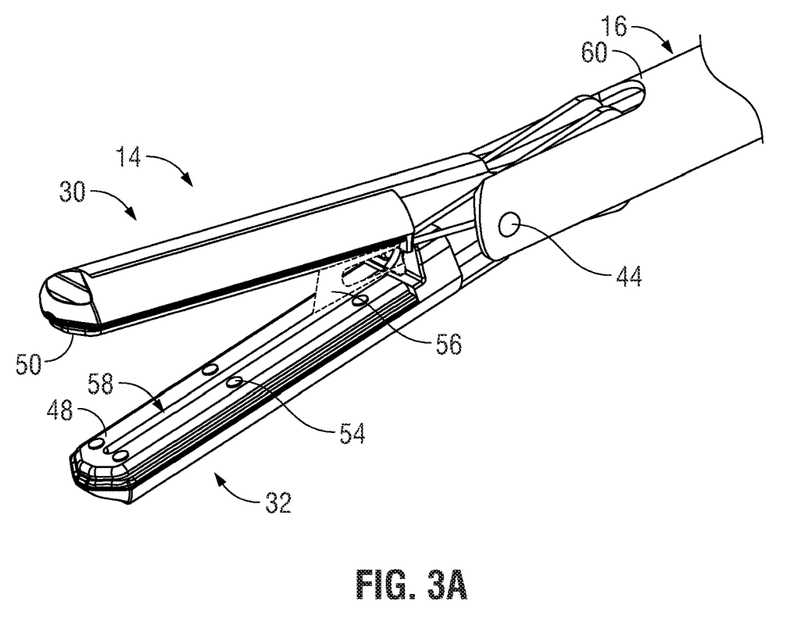
FIG. 3A is an enlarged perspective view of the end effector of FIG. 1 depicted with a pair of jaw members in an open configuration.
Figure 3B:
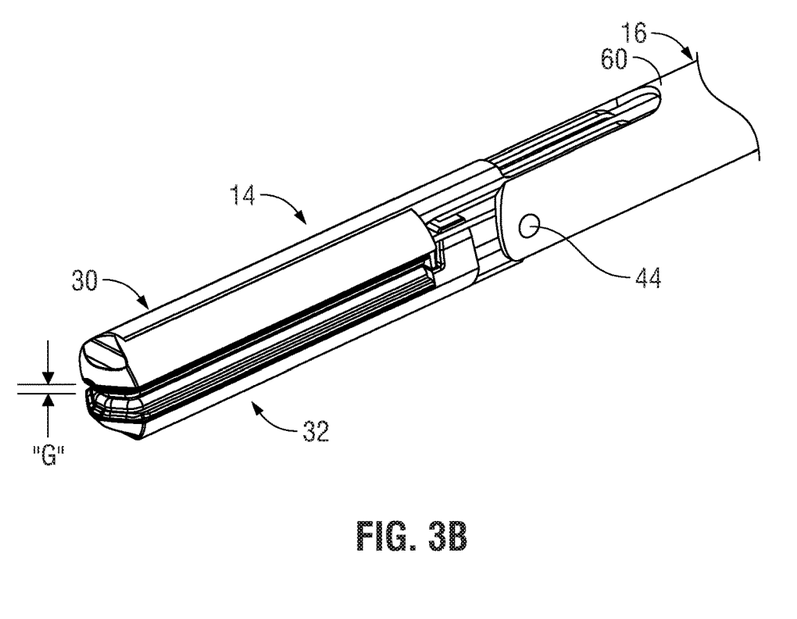
FIG. 3B is an enlarged perspective view of the end effector of FIG. 1 depicted with the pair of jaw members in a closed configuration.

Referring now to FIGS. 3A and 3B, the end effector 14 may be moved from the open configuration (FIG. 3A) wherein tissue (not shown) is received between the jaw members 30, 32, and the closed configuration (FIG. 3B), wherein the tissue is clamped and sealed. Upper jaw member 30 and lower jaw member 32 are physically or mechanically coupled to the elongated shaft 16 about a pivot pin 44. The jaw members 30, 32 are electrically coupled to cable 42, and thus to the generator 40, (FIG. 3) through wires 46a, 46b, respectively, (FIG. 5) extending through the elongated shaft 16 and the housing 12. The wires 46a, 46b provide an electrical pathway to a pair of electrically conductive, tissue-engaging sealing plates 48, 50 disposed on the lower and upper jaw members 32, 30, respectively. The sealing plate 48 of the lower jaw member 32 opposes the sealing plate 50 of the upper jaw member 30, and, in some embodiments, the sealing plates 48 and 50 are electrically coupled to opposite terminals, e.g., active and return terminals associated with the generator 40. Thus, bipolar energy may be provided through the sealing plates 48 and 50. Alternatively, the sealing plates 48 and 50 and/or the end effector 14 may be configured for delivering monopolar energy to the tissue. In a monopolar configuration, one or both sealing plates 48 and 50 deliver electrosurgical energy from an active terminal, while a return pad (not shown) is placed generally beneath a patient and provides a return path to the opposite terminal, of the generator 40.

The jaw members 30, 32 may be pivoted about the pivot pin 44 to move the end effector 14 to the closed configuration of FIG. 3B wherein the sealing plates 48, 50 provide a consistent pressure to tissue grasped therebetween. In one embodiment, to provide a consistent and effective seal at a pressure from about 3 kg/cm$^2$ to about 16 kg/cm$^2$ is necessary and, in other embodiments, from about 7 kg/cm$^2$ to about 13 kg/cm$^2$. Also, in the closed configuration, a separation or gap distance "G" may be maintained between the sealing plates 48, 50 by one or more stop members 54 disposed on or adjacent the sealing plates 48, 50. The stop members 54 contact opposing surfaces on the opposing jaw member 30, 32 and prohibit further approximation of the sealing plates 48, 50. In one embodiment, to provide a consistent and effective tissue seal, an appropriate gap distance from about 0.001 inches to about 0.006 inches is necessary and, in other embodiments, from about 0.002 inches to about 0.005 inches. The stop members 54 may be constructed of an electrically non-conductive plastic or other material molded onto the jaw members 30, 32, e.g., by a process such as overmolding or injection molding. In other embodiments, the stop members 54 are constructed of a heat-resistant ceramic deposited onto the jaw members 30, 32.

When an appropriate seal pressure is applied to tissue and an appropriate gap distance "G" is maintained, electrosurgical energy is delivered to the tissue through the electrically conductive seal plates 48, 50 to affect a tissue seal. Once a tissue seal is established, a knife blade 56 is advanced through a knife channel 58 defined in one or both jaw members 30, 32 to transect the sealed tissue. Knife blade 56 is depicted in FIG. 3A as extending from the elongated shaft 16 when the end effector 14 is in an open configuration. In some embodiments, a knife lockout may be provided to prevent extension of the knife blade 56 into the knife channel 58 when the end effector 14 is in the open configuration, thus preventing accidental or premature transection of tissue.

Figure 4:
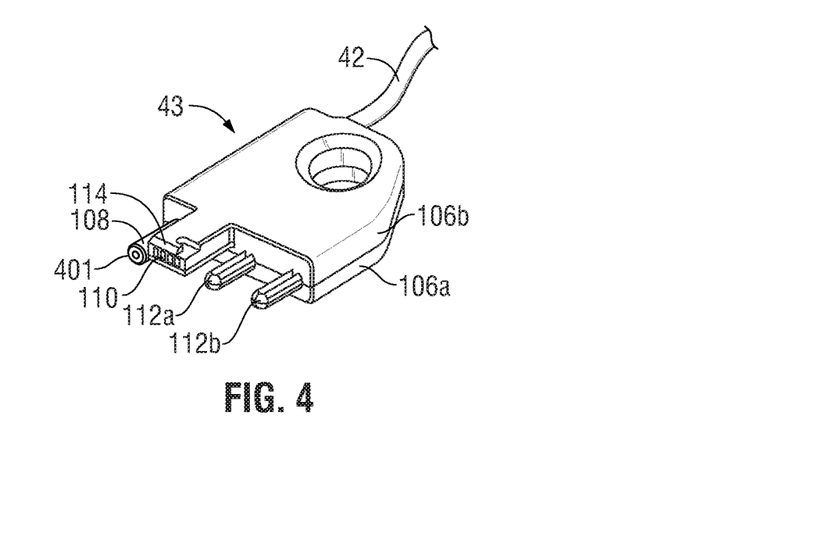
FIG. 4 is a perspective view of a connector according to an embodiment of the present disclosure.
Figure 5:
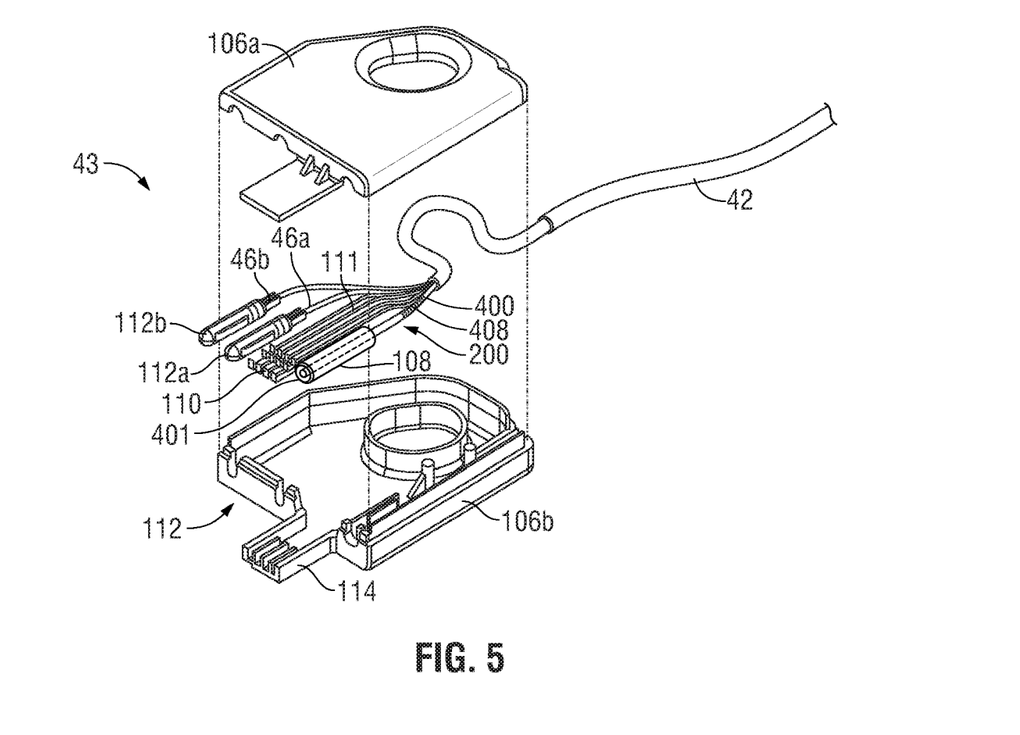
FIG. 5 is an exploded perspective view of the connector of FIG. 4 according to an embodiment of the present disclosure.

With reference to FIGS. 4 and 5, connector 43 is shown coupled to cable 42 and includes a housing portion 106 having a first-half section 106a and a second half-section 106b operatively engagable with one another. Half-sections 106a, 106b are configured and adapted to retain an active pin 112a, a return pin 112b, an optical coupler 108, and a plurality of electrical contacts 110 disposed on a prong 114. The pin 112a is coupled to the wire 46a and the pin 112b is coupled to the wire 46b. The electrical contacts 110 are coupled to control leads 111 which may be coupled to various electrical controls, e.g., switch 36. The optical coupler 108 is connected to an optical fiber 400 at a proximal end 401 of the optical fiber 400. The receptacle 45 includes corresponding connectors for coupling the pins 112a, 112b, contacts 110, and optical coupler 108 to the generator 40, namely, energy-generating components (e.g., RF output stage), sensor circuits, the interrogator 41a, and the controller 41b.

The connector 43 includes an identification assembly 200 including the optical fiber 400, which includes a fiber Bragg grating 408 at a proximal end 401 thereof. The proximal end 401 of the optical fiber 400, which includes the fiber Bragg grating 408, is mounted loosely within the housing 106 of the connector 43 such that strain does not transfer to the fiber 400. In some embodiments, the optical fiber 400 may be thermally insulated (e.g., potting of the housing 106) to prevent thermal effects of the fiber Bragg grating 408. This configuration allows the fiber Bragg grating 408 to be unaffected by thermal and strain imposed on the connector 43. Accordingly, the fiber Bragg grating 408 provides the same feedback when interrogated by the interrogator 41a. The fiber Bragg grating 408 may be individually tailored to encode identification information corresponding to a specific device (e.g., forceps 10). The identification information that may be encoded in the fiber Bragg grating 408 may include, but is not limited to, serial number, model number, usage settings, configuration settings, and the like. Different identification information may be encoded by varying the number, thickness and periodic spacing between reflection points of the fiber Bragg grating 408. The interrogator 41a may interrogate the identification assembly 200 upon insertion of the connector 43 into the receptacle 45. Interrogation may be triggered by detection of the insertion using one or more proximity switches, limit switches, radio frequency tags, and the like.

Figure 6:
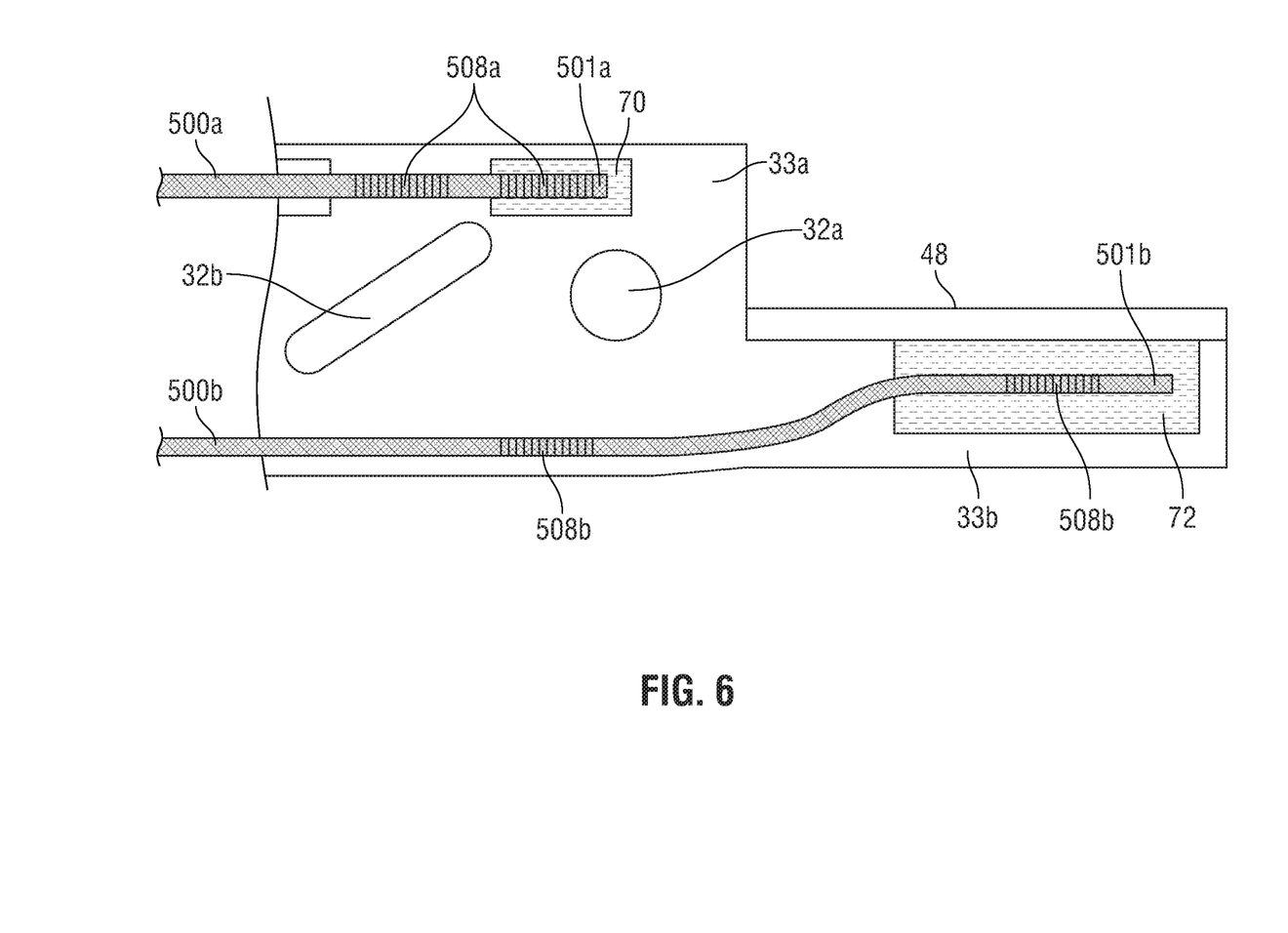
FIG. 6 is a cross-sectional view of a jaw member of FIGS. 3A and 3B according to an embodiment of the present disclosure.

FIG. 6 shows a cross-sectional view of the jaw member 32 including first and second optical fibers 500a and 500b. In some embodiments, the opposing jaw member 30 may also include the optical fibers 500a and 500b. For purposes of simplicity and consistency, use of optical fibers 500a and 500b to monitor temperature and pressure are described hereinbelow with reference to the jaw member 32 only.

The first optical fiber 500a disposed in an upper portion 33a of the jaw member, e.g., above a pivot opening 32a and a cam slot 32b. A second optical fiber 500b is disposed in a lower portion 33b of the jaw member 32 below the sealing plate 48. The optical fibers 500a and 500b include distal ends 501a, 501b, respectively, which are disposed within cavities 70, 72 formed within upper and lower portions 33a, 33b of the jaw member 32. Each of the optical fibers 500a, 500b includes one or more fiber Bragg gratings 508a, 508b disposed within cavities 70, 72, respectively. The cavities 70, 72 may be filled with thermally and electrically conductive material. The material may be a liquid, such as saline. Both of the fiber Bragg gratings 508a, 508b, measure temperature at the jaw member. The fiber 500a is securely mounted within the jaw member 32, e.g., glued thereto along the entire length thereof, to provide strain measurements imposed on the jaw member 32. Strain measurements allow for determination of pressure exerted on the jaw member 32. However, the gratings 508a are affected by both temperature and strain. To obtain accurate strain measurements at the jaw member 32, fiber 500b is mounted in a less secure manner to jaw member 32 (e.g., only at the distal end 501b) such that strain does not transfer to the fiber 500b. This configuration allows the fiber 500b to be affected only by temperature. Thus, the fiber 500a provides sensor feedback regarding temperature and strain to the interrogator 41a while the fiber 500b only provides temperature feedback. The temperature feedback from the fiber 500b is used by the interrogator 41a and/or the controller 41b to determine the temperature at the jaw member 32 and the tissue site as well as the strain by correcting the feedback from the fiber 500a using the feedback from the fiber 500b. The feedback signal from the fiber 500b is used to remove the temperature component of the feedback signal from the fiber 500a to obtain the strain component. The temperature and strain feedback may be used by the controller 41b to control the output of the generator 40. In some embodiments, the adjustments to the output of the generator 40 may include, but are not limited to, changing modes (e.g., cutting, coagulation, sealing), changing power level (e.g., voltage and/or current), duty cycle, terminating energy, and combination thereof. This reading may be provided to the generator 41, which may continuously display the resulting strain readings as pressure imposed on the jaw members 30, 32 and tissue. In some embodiments, the generator 41 may output an indication that a predetermined pressure has been reached. This indication may be used as one of the conditions in determining whether a tissue seal is complete.

Figure 7:
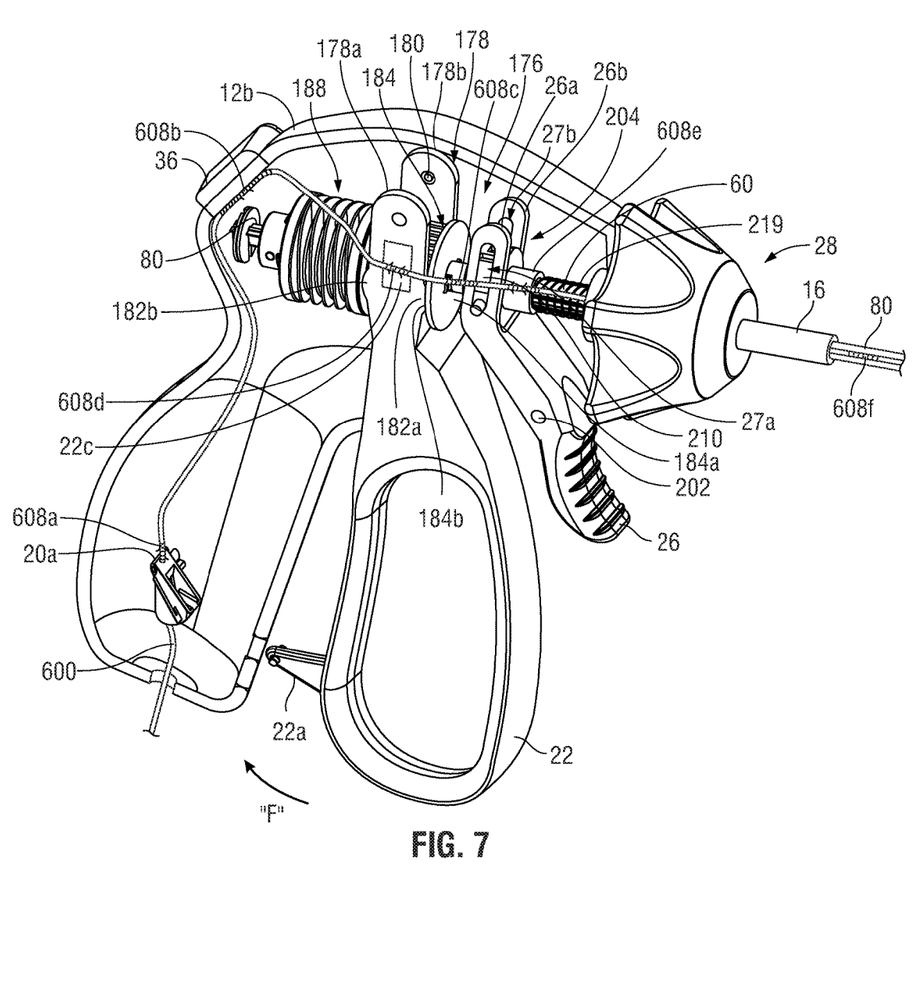
FIG. 7 is a side view of the proximal portion of the forceps of FIG. 1 depicting a movable handle in a separated position with respect to a stationary handle, which corresponds to the open configuration of the end effector, and a knife trigger in a separated configuration with respect to the stationary handle, which corresponds to an un-actuated or proximal configuration of a knife with respect to the jaw members.

Referring now to FIG. 7, operation of the forceps 10 is described. The movable handle 22 may be manipulated to impart longitudinal motion to the jaw drive rod 80, and knife trigger 26 may be manipulated to impart longitudinal motion to the blade 56. As discussed above, longitudinal motion of the jaw drive rod 80 serves to move the end effector 14 between the open configuration of FIG. 3A and the closed configuration of FIG. 3B, and longitudinal motion of the blade 56 serves to move knife blade 56 through knife channel 58 (FIG. 3A).

The movable handle 22 is operatively coupled to an outer shaft member 60 by a connection mechanism 176. The connection mechanism 176 includes a clevis 178, having first and second arms 178a, 178b defined at an upper end of the movable handle 22. The clevis 178 is pivotally supported on the left housing half 12b by a pivot boss 180. Each of two arms 178a, 178b of the clevis 178 extend upwardly about opposing sides of a drive collar 184 and have distal and proximal portions 184a, 184b supported on the outer shaft member 60 and include rounded drive surfaces 182a and 182b thereon. Drive surface 182a engages the distal portion 184a and drive surface 182b engages the distal portion 184b of the drive collar 184. The drive surfaces 182a, 182b are arranged along the longitudinal axis A-A such that pivotal motion of the movable handle 22 about the pivot bosses 180 induce corresponding longitudinal motion of the drive collar 184 along the longitudinal axis A-A, which in turn, provides for longitudinal motion of the jaw drive rod 80. In particular, distal longitudinal motion is imparted to the connection mechanism 176 by pulling the proximal rim 184b of the drive collar 184 with the movable handle 22, as indicated by arrow "F". Distal longitudinal motion of the drive collar 184 is transmitted directly to the jaw drive rod 80 to induce a corresponding distal motion of the jaw drive rod 80, which move the end effector 14 between the open configuration of FIG. 3A and the closed configuration of FIG. 3B.

Referring to FIG. 7, the trigger 26 is pivotally supported in the housing 12 about a pivot boss 202 protruding from the trigger 26. The trigger 26 is operatively coupled to the blade 56 by a knife connection mechanism 204 such that pivotal motion of the trigger 26 induces longitudinal motion of the blade 56. The knife connection mechanism 204 includes upper flanges 26a, 26b of the trigger 26 and a knife collar 210. The upper flanges 26a, 26b include respective slots 27a, 27b defined therethrough that are configured to receive a free end of dowel pin 93, which extends through the knife collar 210 such that pivotal motion of the trigger 26 induces longitudinal motion of the knife collar 210. Dowel pin 93 translates longitudinally within a slot of the outer shaft member 60 and a slot of the jaw drive rod 80 such that longitudinal motion of the knife collar 210 is unimpeded by the dowel pin 93 (not shown).

The knife collar 210 is longitudinally movable over the outer shaft member 60 independently of the motion of the jaw drive rod 80. Thus, the jaw drive rod 80 may be regarded as a stationary reference for the movement of the knife collar 210. The blade 56 is coupled to the knife collar 210 such that the longitudinal motion of the knife collar 210 is transmitted to the blade 56. In particular, the blade 56 translates with the knife collar 210 in both the proximal and distal directions.

The instrument 10 also includes an optical fiber 600 disposed within the housing 12. The fiber 600 is disposed and/or is in contact with various mechanical actuation components of the instrument 10 and is configured to provide for strain measurements and positioning information thereof. In particular, the fiber 600 includes a plurality of fiber Bragg gratings 608 (e.g., 608a, 608b . . . 608n). Each of the gratings 608 is disposed within and/or in contact with the components of the instrument 10. In some embodiments, a plurality of optical fibers 600 may be utilized each having one or more gratings 608. The gratings 608 are used to measure strain and/or position of various mechanical components, as described in further detail below.

The grating 608a is disposed within a lockout member 20a. The movable handle also includes a latch member 22a that is configured to interface with the lockout member 20a disposed within the stationary handle 20. When the movable handle 22 is in the actuated or proximal position, the latch member 22a on the moveable handle 22 is received in the lockout member 20a supported within the stationary handle 20. The lockout member 20a serves to temporarily lock the movable handle 22 in the proximal position against the bias of the spring 188, which biases the movable handle 22. Thus, the lockout member 20a permits the maintenance of pressure at the end effector 14 without actively maintaining pressure on the movable handle 22. The latch member 22a may be released from the lockout member 20a by pivoting the movable handle 22 proximally and releasing the movable handle 22 to move under the influence of the spring 188. Operation of the lockout member 20a is described in greater detail in U.S. patent application Ser. No. 11/595,194 to Hixon et al., now U.S. Pat. No. 7,766,910. In some embodiments (not shown), the latch member 22a and the lockout member 20a may be eliminated to provide an instrument without the temporary locking capability provided by these features.

The grating 608a is impinged by the latch member 22a once the movable handle 22 is approximated toward the stationary handle and the latch member 22a is locked within the lockout member 20a. The strain on the grating 608a is detected by interrogating the fiber 600 by the interrogator 41a. The strain reading may be used to signal that the jaw members 30, 32 are fully clamped. This may be accomplished by outputting an audio and/or visual indication on the generator 40 and/or the instrument 10.

The grating 608b is disposed in contact and/or adjacent to the switch 36. As the switch 36 is toggled, the grating 608b is impinged by the switch 36. The strain is detected by the interrogator 41a. The strain reading is used to signal the generator 40 that the switch 36 is toggled and the generator 40 toggles (e.g., activates or terminates) application of electrosurgical energy. This configuration of the optical fiber 600 obviates the need for an electrical lead and switching contacts.

The grating 608c is disposed in contact with and/or adjacent to the clevis 178 of the movable handle 22. As the movable handle 22 is pivoted about the pivot boss 180, the clevis 178, in particular the arm 178b, pushes against the grating 608c. As the handle 22 is pivoted, the arm 178b moves along the grating 608c while the fiber 600 is continuously interrogated by the interrogator 41a. The continuous strain measurements of the 608c provide position readings of the handle 22, since the grating 608c provides different strain readings based on the exact position thereof being impinged by the movable handle 22. This reading allows for an indication of the degree of approximation between the jaw members 30, 32. This reading may be displayed by the generator 41 and/or used as one of the conditions to indicate that the seal is complete (e.g., ensuring the jaw members 30, 32 are fully approximated).

The grating 608d is disposed within the movable handle 22 as shown by a cutout portion 22c. The portion of the fiber 600 including the grating 608d is secured within or to the movable handle 22, e.g., glued thereto along a portion thereof, to provide for strain measurements imposed on the movable handle 22 during actuation. This allows the interrogator 41a to determine how much pressure is imposed on the handle 22, the jaw drive rod 80, as well as the jaw members 30, 32. This reading may be provided to the generator 41 which may continuously display the resulting strain readings as pressure imposed on the jaw members 30, 32 and tissue. In some embodiments, the generator 41 may output an indication that a predetermined pressure had been reached. This indication may be used as one of the conditions in determining whether a tissue seal is complete.

The grating 608e is disposed in contact with and/or adjacent to one of the upper flanges 26a, 26b. As the trigger 26 is pivoted about the pivot boss 202, the flange 26b pushes against the grating 608e. As the trigger 26 is pivoted, the flange 26b moves along the grating 608e while the fiber 600 is continuously interrogated by the interrogator 41a. The continuous strain measurements of the 608e provide position readings of the trigger 26, since the grating 608c provides different strain readings based on the exact position thereof being impinged by the movable trigger 26. This reading allows for an indication of the degree of extension of the blade 56. This reading may be displayed by the generator 41 and/or used as one of the conditions to indicate that the tissue is fully separated.

The grating 608f is disposed in contact with and/or adjacent the jaw drive rod 80. Grating 608f allows for measurement of the strain forces imposed on the jaw drive rod 80. This reading is indicative of the forces placed on the jaw rod 80 as the movable handle 22 is compressed to approximate the jaw members 30, 32 while grasping tissue. This reading may be used in conjunction with the strain readings from the gratings 608c and 608d, which also provide strain readings regarding actuation of the movable handle 22.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto. Although the foregoing disclosure has been described in some detail by way of illustration and example, for purposes of clarity or understanding, it will be obvious that certain changes and modifications may be practiced within the scope of the appended claims.

What is claimed is:

1. A surgical instrument, comprising:
an end effector;
a first component configured to move the end effector;
a first optical fiber disposed within the end effector and configured to provide a first signal;

a second optical fiber disposed within the end effector and configured to provide a second signal;

a third optical fiber is coupled to the component and configured to provide a third signal; and a controller coupled to the first, second, and third fibers and configured to determine temperature and strain of the end effector based on the first and second signals, respectively, and at least one of strain or position of the component based on the third signal.

2. The surgical instrument according to claim 1, wherein the surgical instrument further includes a second component.

3. The surgical instrument according to claim 2, wherein the third optical fiber includes a first Bragg grating and a second Bragg grating.

4. The surgical instrument according to claim 3, wherein the first Bragg grating is disposed within the first component and the second Bragg grating is disposed within the second component.

5. The surgical instrument according to claim 1, wherein each of the first and second optical fibers includes a Bragg grating.

6. The surgical instrument according to claim 1, wherein the end effector includes a cavity and one of the first optical fiber or the second optical fiber is disposed within the cavity of the end effector.

7. The surgical instrument according to claim 6, wherein the end effector includes a first jaw member and a second jaw member, at least one of the first jaw member or the second jaw member including the cavity.

8. The surgical instrument according to claim 7, wherein the first component is configured to move the first jaw member and the second jaw member relative to one another.

9. The surgical instrument according to claim 6, wherein the cavity contains a thermally and electrically conductive material.

10. The surgical instrument according to claim 9, wherein the electrically conductive material is saline.

11. The surgical instrument according to claim 1, wherein the first signal of the first optical fiber includes a first component corresponding to a temperature measurement.

12. The surgical instrument according to claim 11, wherein the second signal of the second optical fiber includes a first component corresponding to the temperature measurement and a second component corresponding to a strain measurement, and the first component of the first signal is substantially identical to the first component of the second signal.

13. The surgical instrument according to claim 12, wherein the controller configured to determine the strain measurement by removing the first component of the first signal from the second signal.

14. The surgical instrument according to claim 1, wherein the first optical fiber is unsecuredly mounted within the end effector, and the second optical fiber is securedly mounted within the end effector.

* * * * *